(12) United States Patent
Chisholm et al.

(10) Patent No.: US 10,845,361 B2
(45) Date of Patent: Nov. 24, 2020

(54) FORMULATIONS COMPRISING MERCURY-CONTAINING REAGENTS FOR DETECTING DISEASE

(71) Applicant: ATH (AUSTRALIA) PTY LTD, Carlingford (AU)

(72) Inventors: Allan J Chisholm, Carlingford (AU); Nicolas De Luca, Longueville (AU)

(73) Assignee: ATH (AUSTRALIA) PTY LTD, Carlingford (AU)

( * ) Notice: Subject to any disclaimer, the term of this patent is extended or adjusted under 35 U.S.C. 154(b) by 83 days.

(21) Appl. No.: 15/548,767

(22) PCT Filed: Feb. 5, 2016

(86) PCT No.: PCT/AU2016/050067
§ 371 (c)(1),
(2) Date: Aug. 4, 2017

(87) PCT Pub. No.: WO2016/123673
PCT Pub. Date: Aug. 11, 2016

(65) Prior Publication Data
US 2018/0031544 A1    Feb. 1, 2018

(30) Foreign Application Priority Data

Feb. 5, 2015 (AU) .............................. 2015900347

(51) Int. Cl.
*G01N 33/00* (2006.01)
*G01N 33/52* (2006.01)
(Continued)

(52) U.S. Cl.
CPC ............ *G01N 33/52* (2013.01); *G01N 21/78* (2013.01); *G01N 33/574* (2013.01); *G01N 33/6812* (2013.01)

(58) Field of Classification Search
CPC ...................................................... G01N 33/52
(Continued)

(56) References Cited

U.S. PATENT DOCUMENTS

| | | |
|---|---|---|
| 3,434,801 A | 3/1969 | Scherr |
| 3,895,914 A | 7/1975 | Alberty et al. |

(Continued)

FOREIGN PATENT DOCUMENTS

| | | |
|---|---|---|
| CA | 2329322 A1 | 6/2002 |
| CN | 1109590 A | 10/1995 |

(Continued)

OTHER PUBLICATIONS

PCT/AU2016/050067 International Search Report and Written Opinion, dated 2016.
(Continued)

*Primary Examiner* — Christine T Mui
*Assistant Examiner* — Emily R. Berkeley
(74) *Attorney, Agent, or Firm* — JCIP; Joseph G. Chu; Jeremy I. Maynard (57) ABSTRACT

Disclosed herein is a formulation for detecting a species indicative of a disease in a patient. The formulation comprises a mercury-containing reagent which, when contacted with a fluid sample from the patient, colourimetrically indicates whether the fluid sample contains the species. The mercury-containing reagent is contained within a non-flowing carrier which, upon exposure to the fluid sample, causes rapid mixing of substantially all of the mercury-containing reagent and the fluid sample.

14 Claims, 1 Drawing Sheet

(51) Int. Cl.
*G01N 33/574* (2006.01)
*G01N 33/68* (2006.01)
*G01N 21/78* (2006.01)

(58) Field of Classification Search
USPC .......................................................... 436/98
See application file for complete search history.

(56) References Cited

U.S. PATENT DOCUMENTS

| | | | |
|---|---|---|---|
| 4,163,039 A | 7/1979 | Emrich | |
| 5,066,601 A | 11/1991 | Kweon | |
| 5,094,836 A | 3/1992 | Kim | |
| 2004/0018228 A1* | 1/2004 | Fischell | A61B 17/06166 424/450 |
| 2006/0198878 A1 | 9/2006 | Krumme et al. | |
| 2009/0311142 A1 | 12/2009 | Burgess-Cassler et al. | |

FOREIGN PATENT DOCUMENTS

| | | |
|---|---|---|
| CN | 1189619 A | 8/1998 |
| CN | 1407888 A | 4/2003 |
| CN | 102004103 A | 4/2011 |

OTHER PUBLICATIONS

Udenfriend, S. and Cooper, J.R. "The chemical estimation of tyrosine and tyramine" J. Bio. Chem. (1952) vol. 196, pp. 227-233.
Howard, A.N. and Wild, F. "The reactions of diazonium compounds with amino acid and proteins" Biochem. J. (1957) vol. 65, No. 4, pp. 651-659.
English Translation of Chinese Examiner's Report for Chinese Patent Application 201680016742.0, dated 2018.
Extended European Search Report for European Patent Application 16746008.8-1111/3254112, dated 2018.

* cited by examiner

FORMULATIONS COMPRISING MERCURY-CONTAINING REAGENTS FOR DETECTING DISEASE

TECHNICAL FIELD

The present invention relates to a formulation, kit and method for detecting a species indicative of a disease in a patient. In a particular embodiment, the present invention relates to a formulation, kit and method for detecting tyrosine or its metabolites in a patient's urine.

BACKGROUND ART

The presence of certain species in a person's bodily fluids can often be indicative of that person having a disease or condition. Early diagnosis of such a disease or condition can dramatically increase the likelihood of any treatment regimen being successful, and it is an ongoing challenge in the medical field to develop new early diagnosis tests. Such early diagnosis tests are preferably relatively simple to perform and provide reliable results relatively quickly.

Tests for colorectal cancer such as the faecal occult blood (FOB) test, for example, are available. However, the FOB test relies on a patient's faeces containing blood (from a bleeding polyp), which does not occur all the time and is therefore prone to false negatives. Indeed, some reports have indicated that the sensitivity of the FOB test for detecting colorectal cancer is at best 25%. The FOB test also requires a faecal sample to be collected, with many tests not being completed due to patients being reluctant to obtain faecal samples (less than 20% of the FOB kits freely supplied to Australians aged 50-75 are returned). Furthermore, once obtained, the faecal sample needs to be analysed in a laboratory, which complicates the procedure and increases its cost.

The presence of phenolic compounds such as tyrosine and its metabolites in a patient's urine can be indicative of the patient having a cancer, for example, colorectal cancer. Tests for tyrosine and its metabolites using Millon's Reagent or variations thereof are known. Millon's Reagent is obtained by dissolving metallic mercury in nitric acid and diluting with water. When Millon's Reagent is exposed to a fluid sample containing phenolic compounds (e.g. tyrosine and its metabolites), a red-brown precipitate forms. The presence of such a red-brown precipitate following exposure of the patient's urine to Millon's Reagent would prompt the patient to undergo further tests.

As Millon's Reagent contains mercury, it needs to be very carefully handled. Typically, the Millon's Reagent is provided in a glass ampoule with a frangible portion. Immediately before use, the ampoule is broken and the urine sample is added to the Millon's Reagent. However, the broken glass ampoule has sharp edges and presents a health hazard, and there is a risk that the user may be exposed to mercury (e.g. due to spillage). Furthermore, if the ampoule is not broken with a good sharp knock, it may shatter. For at least these reasons, existing tests involving Millon's Reagent are not really suitable for non-specialised use.

U.S. Pat. No. 5,094,836 discloses using an improved form of Millon's Reagent for screening patients for the presence of cancer. The improved form of Millon's Reagent relates mainly to providing a mixed Hg—Ni composition, which improves the stability of the coloured precipitate formed in the presence of tyrosine. U.S. Pat. No. 5,094,836 also discloses that the composition may be admixed with a material to form a gel, with the resultant jelly phase advantageously reducing the hazardous conditions posed by a mercury-containing solution. However, it is acknowledged that the reactive sensitivity of the jelly is apt to decline somewhat compared to that of the solution and, in the examples provided, it was noted that precipitates only formed at the boundary of the jelly and urine phases.

SUMMARY OF INVENTION

In a first aspect, the present invention provides a formulation for detecting a species indicative of a disease in a patient. The formulation comprises a mercury-containing reagent which, when contacted with a fluid sample from the patient, colourimetrically indicates whether the fluid sample contains the species. The mercury-containing reagent is contained within a non-flowing carrier which, upon exposure to the fluid sample, causes rapid mixing of substantially all of the mercury-containing reagent and the fluid sample.

In some embodiments, the non-flowing carrier may, for example, be (or comprise) a gel carrier which, upon exposure to the fluid sample, rapidly disintegrates to release substantially all of the mercury-containing reagent. In alternative embodiments, the non-flowing carrier may, for example, be (or comprise) an absorbent material which, upon exposure to the fluid sample, rapidly absorbs the fluid sample.

The inventor recognised that providing the mercury-containing reagent in a non-flowing carrier such as a gel carrier or an absorbent material has a number of advantages, particularly user safety, but that these advantages must not be at the expense of preventing substantially all of the mercury-containing reagent from being able to rapidly mix with the fluid sample upon exposure to the fluid sample. Experiments have shown, for example, that reactions which occur only at the boundary of jelly and urine phases are far more prone to false (positive or negative) results. The inventor recognised that unless the mercury-containing reagent and fluid sample are able to intimately mix relatively quickly, then the risk of false or inconclusive results is of concern. Embodiments of the present invention provide a very selective and reliable test for the presence of species indicative of a disease in a fluid sample from a patient.

As would be appreciated, rapid disintegration of the gel carrier very quickly results in a vast majority of the mercury-containing reagent being available to react with any species in the patient's fluid sample, thereby providing for an almost as rapid and precise analysis as that which occurs when the mercury-containing reagent is provided in liquid form. The inventor realised that if the gel carrier does not rapidly disintegrate, then there is a significant risk that the reactions which occur and colourimetrically indicate the presence of the species will either not occur to an extent sufficient to be visually detectable or that they will occur only in dispersed portions of the mixture, further hindering visual detection of the colour change.

Similarly, rapid absorption of the fluid sample by the absorbent material very quickly results in a vast majority of the mercury-containing reagent being available to react with any species in the patient's fluid sample, thereby providing for an almost as rapid and precise analysis as that which occurs when the mercury-containing reagent is provided in liquid form.

In some embodiments, the fluid sample is a urine sample from a patient. Urine samples are relatively easy to obtain, especially by the patient themselves, which makes detecting the species indicative of a disease easier from a logistical point of view. Patients also tend to be more receptive to collecting urine samples than faecal samples, so urine testing would therefore be expected to result in a greater degree of patient compliance and hence completed tests. Patients may even be able to self-test for the presence of species indicative of a disease in their urine.

In some embodiments, the species indicative of a disease in a patient is tyrosine (or one or more of its metabolites). As noted above, tyrosine and its metabolites have been found to be elevated in the urine of patients having tumours, especially tumours associated with gastrointestinal cancers such as colorectal cancer (although other malignant tumours can also result in tyrosine and its metabolites or metabolites of tryptophan being elevated in a patient's urine, as discussed below). A positive test using embodiments of the present invention would prompt the patient to seek more specialised medical advice.

In some embodiments, the gel carrier rapidly disintegrates to release substantially all of the mercury-containing reagent within less than about 1 minute after being exposed to the fluid sample. In some embodiments, the absorbent material absorbs the fluid sample within less than about 1 minute after being exposed to the fluid sample.

In some embodiments, the gel carrier is a substance that is miscible in, dissolves in or otherwise rapidly disperses when exposed to the fluid sample. In some embodiments, for example, the gel carrier may be (or may comprise) a hydrogel. In some embodiments, the gel carrier may be formed from any one of the following: polyacrylamides, carboxy methylcellulose, polyvinyl alcohol, poly(acrylamide-co-maleic acid), poly(vinylpyrrolidone), alginates, carbomers, polyoximers, natural and synthetic gums, and mixtures thereof. In embodiments where the gel carrier includes mixtures of substances, the substances can be selected to provide a resultant gel carrier with improved properties (e.g. improved disintegration properties, reduced interactions with specific mercury-containing reagents, better stability in highly acidic conditions, etc.).

In some embodiments, the absorbent material may be (or may comprise) a fibrous material. In some embodiments, the absorbent material may be formed from any one of the following: paper pulp, cotton wool, cellulosic fibres, synthetic fibres, super absorbent polymers and polyvinyl alcohol fibres. In some embodiments, combinations of materials may be used in order to provide an absorbent material having improved properties.

In some embodiments, the mercury-containing reagent comprises mercury salts dissolved in an acid solution (e.g. comprising one or more mineral acids). Such a reagent is known as Millon's Reagent which, as noted above, has been used to detect phenolic compounds such as tyrosine and its metabolites. The production of a red-brown colouration or precipitate when the formulation of the present invention and fluid sample from the patient are mixed is indicative of the presence of tyrosine (and/or its metabolites) in the sample. As discussed above, the presence of significant quantities of tyrosine (and/or its metabolites) in a patient's urine can be indicative of cancer, and a positive test using embodiments of the present invention should prompt the patient to seek more specialised healthcare.

In some embodiments, the mercury-containing reagent may contain additional components. Such additional components, and the advantageous properties they impart on the resultant formulation, will be discussed in further detail below.

In some embodiments, the formulation may further comprise agents such as dispersing agents, solubilising agents, wetting agents or emulsifying agents to improve (or advantageously alter) properties of the gel carrier (e.g. its disintegration properties) or the absorbent material (e.g. its absorbing properties). Any such additional agents are also carried in the non-flowing carrier. The advantageous properties they impart on the resultant formulation will be discussed in further detail below.

In a second aspect, the present invention provides a formulation for detecting a species indicative of a disease in a patient. The formulation comprises a mercury-containing reagent which, when contacted with a fluid sample from the patient, colourimetrically indicates whether the fluid sample contains the species. The formulation also comprises a gel carrier in which the mercury-containing reagent is contained but which, upon exposure to the fluid sample, rapidly disintegrates to release substantially all of the mercury-containing reagent.

In a third aspect, the present invention provides an absorbent pad for detecting a species indicative of a disease in a patient. The pad comprises an absorbent material adapted to rapidly absorb a fluid sample from the patient. The absorbent material contains a mercury-containing reagent capable of colourimetrically indicating whether the fluid sample from the patient contains the species upon contact with the fluid sample. Upon exposure of the pad to the fluid sample, the absorbent material rapidly absorbs the fluid sample, thereby causing rapid mixing of substantially all of the mercury-containing reagent and the fluid sample.

Embodiments of the second and third aspects of the present invention may be as described herein with respect to the first aspect of the present invention in which the non-flowing carrier is a gel carrier and an absorbent material, respectively.

In a fourth aspect, the present invention provides a kit for detecting a species indicative of a disease in a patient. The kit comprises a mercury-containing reagent which, when contacted with a fluid sample from the patient, colourimetrically indicates whether the fluid sample contains the species, and a non-flowing carrier in which the mercury-containing reagent is contained but which, upon exposure to the fluid sample, causes rapid mixing of substantially all of the mercury-containing reagent and the fluid sample. The kit also comprises a container in which the non-flowing carrier and the mercury-containing reagent is contained.

Embodiments of the mercury-containing reagent and non-flowing carrier in the kit of the fourth aspect of the present invention may be as described herein with respect to the first aspect of the present invention.

In some embodiments, the container may be adapted to receive the fluid sample from the patient. In some embodiments, the container may be adapted to receive a predetermined volume of the fluid sample from the patient.

Advantageously, embodiments of the kit of the present invention may be provided in a form simple, safe and reliable enough for use by patients at home (e.g. with a urine sample), with instructions provided with the kit emphasising the importance of the patient seeking specialised medical advice in the event of the kit displaying a positive result.

In some embodiments, the container may comprise a plurality of cells, with at least one of the plurality of cells containing the non-flowing carrier and the mercury-containing reagent; and at least one other of the plurality of cells containing a control sample of the non-flowing carrier that does not contain the mercury-containing reagent. The plurality of cells are configured to allow a visual comparison of the colour in each of the plurality of cells.

In such embodiments, a direct visual comparison can be made between at least two of the cells in the container in order to provide an even more reliable result because factors such as the colour of a patient's urine (for example) or potential colour blindness of the patient (or person assessing the results) are accounted for.

In a fifth aspect, the present invention provides a method of detecting a species indicative of a disease in a patient. The method comprises exposing a fluid sample from the patient to the formulation according to the first or second aspect of the present invention, the absorbent pad of the third aspect of the present invention or the kit of the fourth aspect of the present invention to form a mixture; and observing a colour of the mixture to determine whether the fluid sample contains the species.

In a sixth aspect, the present invention provides a kit for detecting a species indicative of a disease in a patient. The kit comprises a container containing the formulation according to the first or second aspect of the present invention and adapted to receive a fluid sample from the patient. In some embodiments, the kit may also comprise a colour chart for assessing whether the fluid sample contains the species.

In a seventh aspect, the present invention provides the formulation according to the first or second aspect of the present invention or a kit of the third or fifth aspect of the present invention for use in detecting a species indicative of a disease in a patient.

BRIEF DESCRIPTION OF THE DRAWINGS

Specific embodiments of the present invention will be described below with respect to the accompanying drawing, in which.

DESCRIPTION OF EMBODIMENTS

As noted above, the present invention provides formulations for detecting a species indicative of a disease in a patient.

In a first aspect, the formulation comprises a mercury-containing reagent which, when contacted with a fluid sample from the patient, colourimetrically indicates whether the fluid sample contains the species. The mercury-containing reagent is contained within a non-flowing carrier which, upon exposure to the fluid sample, causes rapid mixing of substantially all of the mercury-containing reagent and the fluid sample.

In a second aspect, the formulation comprises a mercury-containing reagent which, when contacted with a fluid sample from the patient, colourimetrically indicates whether the fluid sample contains the species. The formulation also comprises a gel carrier in which the mercury-containing reagent is contained but which, upon exposure to the fluid sample, rapidly disintegrates to release substantially all of the mercury-containing reagent.

The present invention also provides an absorbent pad (or mat) for detecting a species indicative of a disease in a patient. The pad comprises an absorbent material adapted to rapidly absorb a fluid sample from the patient. The absorbent material contains a mercury-containing reagent capable of colourimetrically indicating whether the fluid sample from the patient contains the species upon contact with the fluid sample. Upon exposure of the pad to the fluid sample, the absorbent material rapidly absorbs the fluid sample, thereby causing rapid mixing of substantially all of the mercury-containing reagent and the fluid sample.

The formulations and absorbent pad of the present invention can be used to detect a species indicative of a disease in a patient. Any species that can be detected colourimetrically by exposure to a mercury-containing reagent may be detected using the formulation of the present invention.

In one class of embodiments, the species indicative of a disease in a patient is tyrosine (4-hydroxyphenylalanine) and/or its metabolites. The presence of elevated quantities of tyrosine (and/or its metabolites) in a fluid sample obtained from a patient can be indicative of the patient having tumours, especially tumours associated with gastrointestinal cancers such as colorectal cancer. Tyrosine is used by cells to synthesise proteins, and elevated levels of tyrosine (and/or its metabolites) in the patient's fluid sample can be indicative of their body producing a larger than usual number of cells, as is often the case with fast-growing tumours. Other tumours which might cause elevated quantities of tyrosine in a patient's fluid sample include prostate cancer, ovarian cancer, bladder cancer, breast cancer, cervical cancer, stomach cancer, lung cancer, laryngeal cancer, oesophageal cancer, biliary cancer, hepatoma, duodenal cancer, bronchogenic cancer and bone marrow cancer. In some embodiments, the species indicative of a disease in a patient may also include metabolites of tryptophan, such as 5-hydroxytryptamine (serotonin) and 5-hydroxyindoleacetic acid (5-HIAA). Cancer cells metabolise large amounts of tryptophan and the presence of elevated levels of tryptophan metabolites in a patient's fluid sample may be indicative of cancer.

This class of embodiments is described in further detail below, but it is important to recognise that the present invention is not limited to detecting only tyrosine or its metabolites and, in some embodiments, metabolites of tryptophan. For example, it is envisaged that embodiments of the present invention may also be used to detect raised levels of urinary nucleosides such as pseudouridine, 2-pyridone-5-carboxamide-N1-ribofuranoside, N2,N2-dimethylguanine, 1-methylguanosine, 2-methylguanosine and 1-methyladenosine, the presence of which in fluid samples from patients may be used for early detection and clinical diagnosis of cancers such as colorectal, gastric, liver, lung and breast cancers.

In one class of embodiments, the fluid sample is a urine sample from the patient. As noted above, urine samples are relatively easy to obtain and often contain species indicative of a disease in a patient. Typically, the urine sample is obtained mid-stream (any potential contaminants will generally be present in a patient's initial urine stream) from the patent's first pass urination in the morning (which contains the highest concentration of markers). This class of embodiments is described in further detail below, but it is important to recognise that the present invention is not limited to detecting the species in only urine. For example, it is envisaged that embodiments of the present invention may be used to detect the species in saliva, blood and, despite the collection issues discussed above, faecal matter.

The formulation comprises a mercury-containing reagent which, when contacted with a fluid sample from the patient, colourimetrically indicates whether the fluid sample contains the species. That is, when the fluid sample is mixed with the mercury-containing reagent, a reaction that results in a colour change occurs. The reaction may, for example, result in the formation of a coloured precipitate. Alternatively (or in addition), the reaction may result in a colour change of the mixture.

In some embodiments, the mercury-containing reagent may comprise mercury dissolved in an acid solution. Such a reagent is known as Millon's Reagent which, as noted above, has reliably been used to detect phenolic compounds (such as tyrosine) in fluid samples for many years. The acid solution is typically a mineral acid (preferably a strong mineral acid), such as nitric acid, sulphuric acid, or a combination thereof.

In some embodiments, the mercury-containing reagent may comprise different forms of mercury (e.g. salts having different oxidation states like $Hg^+$ and $Hg^{2+}$) or additional components, which impart advantageous properties to the reagent or which make it more suitable for detecting a particular species. For example, the mercury-containing reagent may comprise a source of $Hg^+$ ions and a source of $Hg^{2+}$ ions (e.g. mercury(II) sulphate and mercurous nitrate), typically in an acid solution. Such a reagent is an improved form of Millon's Reagent, and has a greater sensitivity to tyrosine and its metabolites. Any precipitates that form may also be more stable than would be the case for reagents containing just $Hg^+$.

In some embodiments, for example, the mercury containing reagent may comprise between about 10 and 90 wt % mercury, for example, between about 20 and 80 wt %, between about 30 and 70 wt %, between about 40 and 60 wt % mercury. In some embodiments, for example, the mercury containing reagent may comprise about 10 wt %, 20 wt %, 30 wt %, 40 wt %, 50 wt %, 60 wt %, 70 wt %, 80 wt % or 90 wt % mercury. In embodiments where the mercury containing reagent comprises $Hg^+$ and $Hg^{2+}$, the ratio of $Hg^-:Hg^{2+}$ may be from 0.1 to 1:0.1 to 1.0.

The mercury-containing reagent may also include a source of $Ni^{2+}$ ions, for example a nickel salt such as nickel sulphate, in order to improve the stability of the precipitate that forms in the presence of the species, and thereby improve the reliability of the test (precipitates having enhanced stability are more likely to reliably form and, once formed, last for longer, therefore making them easier to visually detect). If present, the mercury containing reagent may include nickel in an amount of between about 0.1 to 0.5 parts by weight to 1 part by weight mercury.

The mercury-containing reagent may also include a source of $Cd^{2+}$ ions, for example a cadmium salt such as cadmium sulphate, in order to improve the stability of the precipitate that forms in the presence of the species and thereby improve the reliability of the test. If present, the mercury containing reagent may include cadmium in an amount of between about 0.05 to 0.5 parts by weight to 1 part by weight mercury.

In embodiments where the species being detected includes tyrosine or its metabolites and, optionally, metabolites of tryptophan the mercury-containing reagent may also include a compound such as 1-nitroso-2-naphthol. 1-nitroso-2-naphthol complexes with 4-hydroxylated phenolic acids such as tyrosine and the tryptophan metabolites serotonin and 5-HIAA to form a product having a red colour (the product is a different product to that formed when the species indicative of a disease reacts with the mercury-containing reagent). Elevated levels of 5-HIAA in patient's fluid samples (especially urine samples) are well documented in gastrointestinal tumours, and the presence of 1-nitroso-2-naphthol in the mercury-containing reagent may therefore help to enhance the sensitivity of the formulation to detecting species indicative of a disease. If present, the mercury containing reagent may include 1-nitroso-2-naphthol in an amount of between about 0.05 to 0.5 parts by weight to 1 part by weight mercury.

The mercury-containing reagent may also include diazonium compounds, such as benzenediazonium chloride, 2,4-dichloroaniline diazonium salts, 2,6-dichlorobenzene-diazonium-tetrafluoroborate and p-nitrobenzene-diazonium-p-toulenesulfonate, which can complex with tyrosine and its metabolites, even under highly acidic conditions, in order to increase the sensitivity of the reagent.

The mercury-containing reagent may also include tetrazonium salts, such as tetrazonium diaminodiphenylamine. Such salts can form a fluorescent red dye in the presence of tyrosine and tryptophan.

The exact composition of the mercury-containing reagent will depend on factors such as the nature of the fluid sample, non-flowing carrier and the species to be detected. It is within the ability of a person skilled in the art to prepare an appropriate mercury-containing reagent for use in the present invention.

The amount or proportion of mercury-containing reagent contained in the formulation or absorbent pad will depend on factors such as the expected concentration of the species in the sample, the volume of the sample, the form of the non-flowing carrier, etc. It is within the ability of a person skilled in the art to estimate the amount or proportion of mercury-containing reagent required for any given formulation or absorbent pad and, if necessary, conduct routine tests to determine if the estimated proportion is appropriate.

In embodiments where the non-flowing carrier is a gel, for example, the formulation may comprise between about 20 and about 80 vol %, e.g. between about 30 and about 70 vol %, between about 40 and about 60 vol %, between about 30 and about 80 vol %, between about 50 and about 80 vol %, of the mercury-containing reagent. In some embodiments, the formulation may comprise about 20 vol %, about 30 vol %, about 40 vol %, about 50 vol %, about 60 vol %, about 70 vol % or about 80 vol % of the mercury-containing reagent.

In some embodiments, for example, the formulation or absorbent pad may comprise between about 0.01 and about 5 mL, between about 0.5 and about 3 mL, between about 1 and about 2 mL or between about 0.5 and about 1.5 mL (e.g. about 1 mL) of the mercury-containing reagent.

Gel Carrier

In some embodiments of the present invention, the mercury-containing regent is contained within a gel carrier. The mercury-containing reagent is safely contained within the gel carrier during normal storage and handling conditions. Upon exposure to the fluid sample, however, the gel carrier is adapted to rapidly disintegrate and release substantially all of the mercury-containing reagent. The gel carrier may disintegrate, for example, because it is miscible in the fluid sample. The gel carrier may disintegrate, for example, because it dissolves in the fluid sample. The gel carrier may disintegrate, for example, because it disperses into the fluid sample.

The gel carrier must rapidly disintegrate in order to rapidly release substantially all of the mercury-containing reagent, so that it can then react with the species (if present) in the patient's fluid sample. In some embodiments, for example, it is envisaged that determining whether the sample contains the species will take about 5 minutes. Thus, in order for the mercury-containing reagent to have time to react with the species (if present) to produce its colorimetric response, a substantial portion of the mercury containing reagent must be released from the gel (so it can react with the species) in significantly less than 5 minutes. The time taken for the gel carrier to disintegrate will depend on factors such as the relative volumes of the fluid sample and gel carrier, the nature of the fluid sample, the acidity of the mercury-containing reagent, etc. It is envisaged, however, that substantially all of the mercury-containing reagent would ideally be released within less than about 1-3 minutes (e.g. 1-2 min) after exposure to the fluid sample. In some embodiments, the time taken for the gel carrier to disintegrate after exposure to the fluid sample is about 180 seconds, about 150 seconds, about 120 seconds, about 90 seconds, about 60 seconds or about 30 seconds.

Whilst it will depend on many factors, in the context of the present invention, "substantially all of the mercury-containing reagent" is intended to mean more than about 80%, 85%, 90% or 95% of the mercury-containing reagent contained in the gel carrier is released within the specified time.

The gel carrier may be formed from any substance or combination of substances, provided that it is capable of forming a semi-solid immobile (substantially non-flowing) gel that can carry the mercury-containing reagent (noting that, in some embodiments, this may be highly acidic) for an appropriate storage time, but which will rapidly disintegrate to release substantially all of the mercury-containing reagent upon exposure to the fluid sample. Despite having to rapidly disintegrate upon exposure to the fluid sample, the gel carrier must, in normal handling and use, allow very little (if any) mercury to escape. It is within the ability of a person skilled in the art, using the teachings provided herein and routine experiments, to determine whether a particular gel carrier is suitable for use in the present invention.

Whilst the gel does not need to be a solid and may have some flowing ability, it must be sufficiently viscous so that it is not able to readily flow at temperatures expected to be encountered in normal use, even in the event of a container containing the formulation being accidentally knocked over. For example, in some embodiments, the gel carrier may have a viscosity ranging from about 50,000 to about 1,000,000 cps at ambient temperature. The viscosity of the gel carrier may, for example be about 50,000 cps, about 100,000 cps, about 150,000 cps, about 200,000 cps, about 250,000 cps, about 300,000 cps, about 350,000 cps, about 400,000 cps, about 450,000 cps, about 500,000 cps, about 550,000 cps, about 600,000 cps, about 650,000 cps, about 700,000 cps, about 750,000 cps, about 800,000 cps, about 850,000 cps, about 900,000 cps, about 950,000 cps or about 1,000,000 cps.

The gel carrier may be a substance that rapidly disintegrates (e.g. disperses) when exposed to an aqueous solution. One suitable class of substances are hydrogels, which are a network of polymer chains that are hydrophilic, and are highly absorbent (they can contain over 90% water) natural or synthetic polymeric networks. The mercury-containing reagent can be carried within the interstitial spaces defined between the polymer chains.

The inventor has found that not all gels are able to be used in the present invention (i.e. will meet the functional requirements of the gel carrier). Indeed, the present invention relates, at least in part, to the inventor challenging the conventional wisdom that carrying Millon's Reagent in a gel does not work (e.g. as is noted in U.S. Pat. No. 5,094,836), and surprisingly and unexpectedly discovering that mercury-containing reagents such as Millon's Reagent can, in fact be carried by a gel. The inventor realised that substances such as gelatine and agar gels are generally not suitable for use in the present invention, because these are either not stable at low pH or do not rapidly disintegrate upon exposure to the patient's fluid sample. However, the gels specifically disclosed herein are suitable for use in the present invention, and routine tests carried out by a person skilled in the art in light of the teachings of the present invention will indicate the suitability of any given gel carrier for use in the present invention.

In some embodiments, the gel carrier is formed from any one or a combination of polyacrylamides, carboxy methylcellulose, polyvinyl alcohol, poly(acrylamide-co-maleic acid), poly(vinylpyrrolidone), alginates, carbomers, polyoximers, natural and synthetic gums. In embodiments where the gel carrier includes a combination of substances, those substances can be selected to provide a resultant gel carrier with improved disintegration properties, reduced likelihood of interactions with specific mercury-containing reagents, increased stability in acidic conditions, or the like. Mixtures of gel-forming substances may also enable better dispersion of interacting components in the formulation and patient's fluid sample, potentially improving the detection of specific target markers.

Specific examples of substances which can be used to form the gel carrier include PVP K30 (a synthetic polyvinylpyrrolidone polymer), PLURONIC F88 (a difunctional block copolymer surfactant terminating in primary hydroxyl groups), PVPP (polyvinylpolypyrrolidone—a highly cross-linked version of PVP), PAM SAP (a polyacrylamide super absorbent polymer) and CMC HV (a high-viscosity, technical-grade sodium carboxymethyl cellulose).

The proportion of gel carrier to mercury-containing reagent in the formulation will depend on factors such as the amount of the mercury-containing reagent to be contained, the expected concentration of the species in the sample, the volume of the sample, etc. It is within the ability of a person skilled in the art to estimate the proportion of gel carrier required for any given formulation and, if necessary, conduct routine tests to determine if the estimated proportion is correct.

In some embodiments, for example, the formulation may comprise between about 0.5 mL to about 2.0 mL of the gel carrier. In some embodiments, for example, the formulation may comprise between about 20 and about 80 vol %, e.g. between about 30 and about 70 vol %, between about 40 and about 60 vol %, between about 30 and about 80 vol %, between about 50 and about 80 vol %, of the gel carrier. In some embodiments, the formulation may comprise about 20 vol %, about 30 vol %, about 40 vol %, about 50 vol %, about 60 vol %, about 70 vol % or about 80 vol % of the gel carrier.

Typically, the gel carrier would be formed shortly after mixing with the mercury-containing reagent (or precursors of the mercury-containing reagent) so that, upon vigorous stirring, a substantially homogeneous dispersion of the mercury-containing reagent within the gel carrier is obtained. In effect, the mercury-containing reagent is admixed with the gel carrier. It will be appreciated, however, that any method which results in the mercury-containing reagent being safely contained within the gel carrier would be suitable.

Absorbent Material

In some embodiments, the mercury-containing regent is contained within an absorbent material which, when exposed to the fluid sample, is adapted to rapidly absorb the fluid sample. Any absorbent material which is capable of remaining stable whilst carrying the (potentially highly acidic) mercury-containing reagent in a secure manner (i.e. with substantially no leakage) during storage, but rapidly absorbing the fluid sample once exposed to it may be used. Ideally, the absorbent material should not chemically or physically change substantially throughout the shelf-life of the formulation. Any change in colour of the mixture postexposure (e.g. when a red precipitate forms) must also be clearly visible to the user, despite any absorbent material that may remain.

The absorbent material may utilise any suitable mechanism to absorb the fluid sample (e.g. capillary action or swelling), provided that it causes rapid absorption of the fluid sample whereupon the fluid sample and mercury-containing regent become well mixed. In some embodiments, for example, the absorbent material may absorb the fluid sample into its matrix, where reactions take place and any resultant colour change is visible in the material itself. In some embodiments, for example, absorbing the fluid sample may cause the absorbent material to release the mercury-containing regent, where any resultant colour change is visible in the supernatant liquid (and possibly contrasted against any remaining absorbent material). In some embodiments, for example, absorbing the fluid sample may cause the absorbent material to swell, dissolve or disintegrate, where any resultant colour change is visible in the resultant liquid.

The absorbent material must rapidly absorb the fluid sample. In some embodiments, for example, it is envisaged that determining whether the sample contains the species will take about 5 minutes. Thus, in order for the mercury-containing reagent to have time to react with the species (if present) to produce its colorimetric response, a substantial portion of the fluid sample must be absorbed by the absorbent material (so any species in the sample can react with the mercury-containing reagent) in significantly less than 5 minutes. The time taken for the absorbent material to absorb the fluid sample will depend on factors such as the relative volume of the fluid sample and size of the absorbent material, the nature of the fluid sample, the acidity of the mercury-containing reagent, etc. It is envisaged, however, that the fluid sample (or at least an appropriate volume thereof) would ideally be absorbed within less than about 1-3 minutes (e.g. 1-2 min) after the absorbent material was exposed to the fluid sample. In some embodiments, the time taken for the absorbent material to absorb the fluid sample is about 180 seconds, about 150 seconds, about 120 seconds, about 90 seconds, about 60 seconds or about 30 seconds.

The absorbent material may, for example, be a fibrous material (e.g. provided as a pad or mat) or a compact powder (e.g. provided as a tablet). The absorbent material may, for example, be formed from any one of the following materials: paper pulp, cotton wool, cellulosic fibres (e.g. bleached hemp and bamboo fibres), synthetic fibres (e.g. in microfiber form so that they absorb via capillary action), super absorbent fibres or polymers (e.g. based on acrylic acid derivatives) polyvinyl alcohol (PVA) fibres, and synthetic or natural fibres containing super absorbing polymers (SAPs). An absorbent material comprising two or more of these materials may also be used.

The absorbent material may be provided in any suitable physical form, for example, fibrous form (e.g. for textile materials), compact form (e.g. for mats or tablets made from compressed powders), sheet form (e.g. for cellulosic materials) or fluff (flock) form. For example, in embodiments where the absorbent material is cotton wool, the cotton wool may be in sheet, woven and/or fluff form. For example, in embodiments where the absorbent material is paper pulp, the paper pulp may be in sheet or fluff pulp form. For example, in embodiments where the absorbent material is PVA, the PVA may be in sheet or fibre form. The super absorbent polymers may be spun to yarn, flock or woven and may be cross linked with sodium acrylate, acrylic acid or methyl acrylate.

The absorbent material may be of any convenient size. For example, in some embodiments, the dimensions of the absorbent material are selected to match those of cells of a test container, such that it can snugly fit therein (as described below).

The amount of mercury-containing reagent carried by the absorbent material will depend on factors such as the expected concentration of the species in the sample, the volume of the sample, etc. It is within the ability of a person skilled in the art to estimate the amount of mercury-containing reagent required for any given formulation as well as the corresponding form, size, density and kind of absorbent material suitable for a particular application. In some embodiments, for example, these parameters may be selected such that the absorbent material can snugly fit into a cell of a test kit (described below), rapidly absorb substantially all of the urine expected to be introduced into the cell and clearly show any resultant colour change.

In some embodiments, for example, the formulation comprises between about 10 and 30 vol % (e.g. between about 15 and 25 vol %, between about 15 and 20 vol % or about 20 vol %) of the total volume of the absorbent material. In some embodiments, between about 0.01 and about 5 mL, between about 0.5 and about 3 mL, between about 1 and about 2 mL or between about 0.5 to about 1.5 mL (e.g. about 1 mL) of the mercury-containing reagent is carried by the absorbent material.

The mercury-containing reagent may be incorporated into the absorbent material in any suitable manner, provided that, once so incorporated, there is substantially no leakage of the mercury containing reagent. Ideally, the absorbent material will be substantially dry, with the mercury containing reagent securely held within the material.

In some embodiments, for example, the absorbent material may be soaked in a solution containing the mercury containing reagent for a period of time sufficient for it to absorb an effective amount of the mercury containing reagent. The absorbent material may then be allowed to dry, ether in air or by heating (provided that the mercury-containing reagent is heat stable).

Other Components

The mercury-containing reagent or formulation of the present invention may also include other components. For example, some embodiments may also include agents such as dispersing agents, solubilising agents, wetting agents or emulsifying agents to improve (or advantageously alter) properties of the gel carrier (e.g. its disintegration properties) or absorbent material (e.g. its absorbing properties). For example:

dispersing agents can help to quickly disperse the mercury-containing reagent throughout the patient's fluid sample, or aid to quickly disperse the gel-carrier;

solubilising agents can help to solubilise components in the formulation and patient's fluid sample, which may enhance any reactions therebetween;

wetting agents can help components in the formulation and patient's fluid sample to mix, which may enhance any reactions therebetween; and emulsifying agents can help slightly immiscible components in the formulation and patient's fluid sample to become more intimately mixed (and hence enhance any reactions therebetween).

The formulations of the present invention may be provided in any convenient form. Given the toxic nature of mercury, however, even though the formulation could be provided in bulk form, it would typically be provided in unit form in order to minimise handling. For example, an appropriate amount (e.g. volume, in the embodiments where the mercury-containing reagent is carried in the gel carrier) of the formulation may be provided in a unit form. Similarly, an appropriate amount (e.g. volume or weight) of the mercury-containing reagent may be provided a unit sized piece of absorbent material. This unit form may, for example, be provided in its own container (e.g. a vial or ampoule) for subsequent use by the patient or medical practitioner administering the test. In some embodiments, the container may be adapted to receive a volume of the fluid sample therein (e.g. so that the appropriate volume of a urine sample can simply be added to the container, the container sealed and then shaken to disintegrate the gel and enable the mercury-containing reagent to react with species in the urine).

The volume of the fluid sample required to detect whether the fluid sample contains the species may vary depending on the nature of the species to be detected, its likely concentration in the patient's fluid sample and other factors either known to a person skilled in the art or readily ascertainable using routine experimentation. In some embodiments, the volume of the fluid sample required to detect whether the fluid sample contains the species may vary between about 50-150% of the volume of the formulation (e.g. the volume of the fluid sample is about 50%, 60%, 70%, 80%, 90%, 100%, 110%, 120%, 130%, 140% or 150% of the volume of the formulation). If the volume of the fluid sample used is too low, then the amount of species present may be too low for detection and/or the gel carrier may not all disintegrate. If the volume of the fluid sample used is too high, then the resultant precipitate may not form or may be too dispersed for detection.

For example, in some embodiments, 2-20 mL of a patient's fluid sample may be mixed with an equivalent volume of the formulation.

Kit

The present invention also provides a kit for detecting a species indicative of a disease in a patient. The kit includes a mercury-containing reagent which, when contacted with a fluid sample from the patient, colourimetrically indicates whether the fluid sample contains the species, and a non-flowing carrier in which the mercury-containing reagent is contained but which, upon exposure to the fluid sample, causes rapid mixing of substantially all of the mercury-containing reagent and the fluid sample. The kit also includes a container in which the non-flowing carrier and the mercury-containing reagent is contained. The mercury-containing reagent and non-flowing carrier in this kit may be as described above.

Any container may be used with the kit, provided the non-flowing carrier and mercury-containing reagent can be stably held therein for its shelf-life (e.g. the container may need to be stable with highly acidic substances). The container may be simply used to house the mercury-containing reagent and non-flowing carrier until the kit is ready for use, whereupon they are transferred to another location. In some embodiments, for example, the container may be the vial or ampoule, as described above. Such vials or ampoules are, however, more suited for use by professional medical personnel and, in alternative embodiments, the container may be adapted to be more "user-friendly", even to the extent of being suitable for use by a patient themselves, as discussed in further detail below.

The container may be adapted to receive the fluid sample from the patient (e.g. by a patient either directly or indirectly urinating onto the container). In some embodiments, for example, the container may be adapted to receive a predetermined volume of the fluid sample from the patient. As would be appreciated, this would help to improve the accuracy and consistency of test results.

As described herein, it would be advantageous to provide a reliable test for use by a patient themselves. As such, embodiments of the kit of the present invention may be provided in a form that is simple enough for patients to use at home (e.g. with a urine sample), with instructions provided with the kit emphasising the importance of the patient seeking specialised medical advice in the event of a positive result.

In some embodiments, the container may comprise a plurality of cells, with at least one of the plurality of cells containing the non-flowing carrier and the mercury-containing reagent; and at least one other of the plurality of cells containing a control sample of the non-flowing carrier that does not contain the mercury-containing reagent. The plurality of cells are configured to allow a visual comparison of the colour in each of the plurality of cells.

In such embodiments, a direct visual comparison can be made between at least two of the cells in the container in order to provide an even more reliable result because factors such as the colour of a patient's urine (for example) or potential colour blindness of the patient (or person assessing the results) are accounted for.

In some embodiments, different amounts of mercury-containing reagent may be contained in each of the plurality of cells which contain the non-flowing carrier and the mercury-containing reagent. After exposure to the patient's fluid sample, the gradation in colour across these cells may provide results indicative of a quantity of the species to be detected (e.g. tyrosine) in the sample, which may be correlatable with a severity of the disease.

Figure 1:
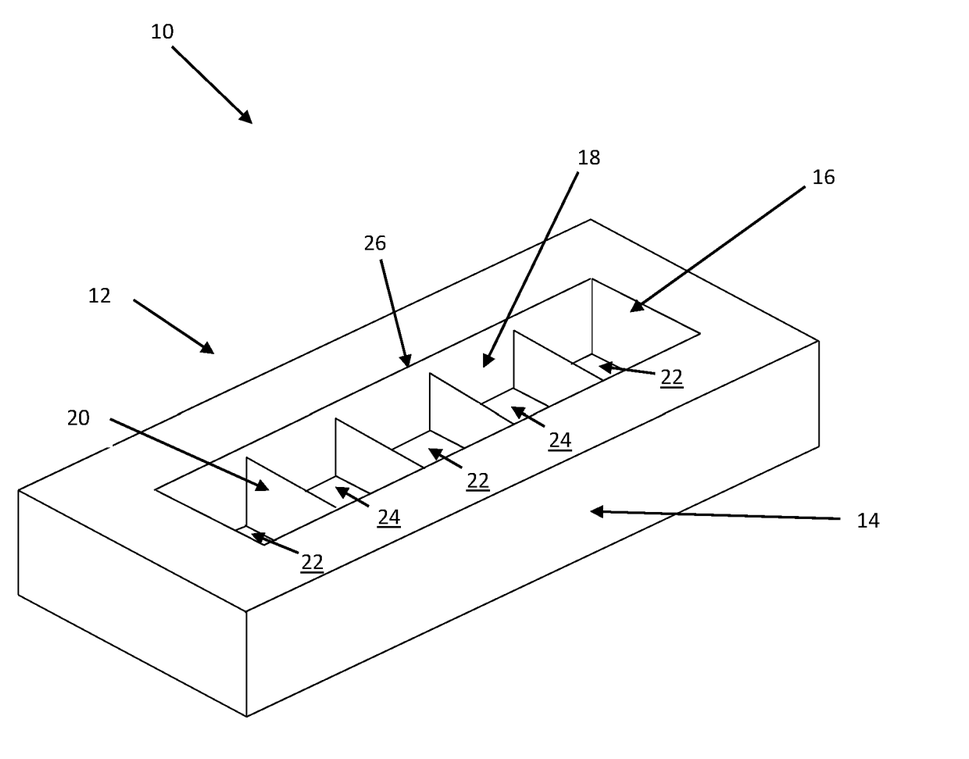
FIG. 1 shows a kit for detecting a species indicative of a disease in a patient in accordance with an embodiment of the present invention.

A specific embodiment of the container for use with the kit of the present invention will now be described with reference to FIG. 1. Shown in FIG. 1 is a test device 10, which has a generally rectangular shape with opposing sides 12, 14 defining gripping portions. The central portion of device 10 includes a recess 16 that is includes five separate cells (about 5 mL in volume) shown generally as 18, which are divided by walls shown generally as 20. Rectangular-shaped pads 22 of an absorbent material into which a mercury-containing reagent has been absorbed are located at the bottom of three of cells 18. The other two cells 18 contain rectangular-shaped pads 24 of the same absorbent material, but which contain no mercury-containing reagent. Each pad 22, 24 is shaped to be snugly received within its respective cell 18, so that it is unlikely to fall out of the device 10, even in the event of the device 10 being tipped upside down. Walls 20 are slightly lower than a rim 26 of the recess 16, for the reasons described below.

In use, a patient would unwrap the device and place it on a stable, flat surface. The patient would then urinate into a separate cup (not shown), filling it to a prescribed level (e.g. as shown by a level indicator on the container). The patient may then hold the device 10 in their hand by gripping the opposing sides 12, 14 and then tip the urine from the cup into the recess 16 which, provided the prescribed amount of urine is in the cup, will fill the recess 16. Preferably, for the reasons discussed above, the urine introduced into the device 10 should be from mid-stream during the patient's first urination of the day. As the walls 20 are slightly lower than the rim 26 of the recess 16, urine will tend to flow from one cell 18 into an adjacent cell 18 before it will reach the level of the rim 26. In this manner, all five cells 18 should become filled with urine before the urine will reach the rim 26, at which time the device 10 is full.

Once full of the patient's urine, the device 10 should be set aside for a prescribed period (e.g. 1-5 mins), during which time the absorbent pads 22, 24 will rapidly absorb the urine. Once the prescribed period has expired, the patient simply tips the remaining urine out of the device 10 and visually examines the colour of absorbent pads 22, 24. The resultant colour of absorbent pads 22 is indicative of whether the patient's urine contains the relevant species (e.g. the pad will have turned a red colour if tyrosine is present in the patient's urine, in embodiments where the device 10 is being used to detect colorectal cancer). The resultant colour of the absorbent pads 24 may be visually contrasted with that of pads 22 in the event of the patient being colour blind or the patient's urine being highly coloured (e.g. as might be the case if the patient is dehydrated, for example).

In some embodiments, the amount of mercury-containing reagent that is in the pads 22 may differ in order to provide a gradation in colour for a positive result, which may provide results indicative of a quantity of the species to be detected (e.g. tyrosine) in the patient's urine. In some embodiments, a colour chart (not shown) may also be provided in order to provide further assistance to the patient in assessing the results.

As noted above, the present invention also provides a method of detecting a species indicative of a disease in a patient. The method comprises exposing a fluid sample from the patient to the formulations, absorbent pad or kit of the present invention, and observing the colour of the resultant mixture to determine whether the fluid sample contains the species.

The fluid sample from the patient may be exposed to the formulation using any suitable technique, but would most commonly involve adding the fluid sample to the formulation and either shaking the resultant mixture (e.g. in embodiments containing a gel carrier) or allowing the resultant mixture to stand (e.g. in embodiments containing an absorbent material) for an appropriate period of time (e.g. 1-2 minutes). The mixture may then be left to stand for an appropriate period of time (e.g. 1-5 minutes), during which the formation of a coloured product (e.g. a red precipitate) is indicative of the presence of the species. In some embodiments, it is envisaged that the entire process could take as little as about 2, 3, 4, 5, 6 or 7 minutes, and could be carried out by the patient themselves.

As discussed above, the fluid sample is typically a urine sample from the patient. If so, the urine sample is preferably obtained mid-stream from the patient's first pass urination. Specialised urine collection devices may be utilised for collecting urine samples from a patient.

Also disclosed herein is a kit for detecting a species indicative of a disease in a patient. The kit comprises a container adapted to receive a fluid sample from the patient, and which already contains (an appropriate amount of) the formulations of the present invention. In some embodiments, the kit may also comprise a colour chart for assessing whether the fluid sample contains the species (i.e. whether the fluid sample is positive or negative to levels of the species indicative of a disease in a patient). In some embodiments, the kit may also comprise a urine collection device, such as that developed by the present applicant, for collecting mid-stream urine samples from a patient.

The present invention provides the formulation according to the first aspect of the present invention for use in detecting a species indicative of a disease in a patient.

EXAMPLES

Example 1A

A formulation in accordance with an embodiment of the present invention was prepared by mixing 2 mL of component (1), 2.4 mL of (2), 0.6 mL of (3) and 0.1 mL of (4), where the components are as follows:
1) 18% solution of mercury sulphate in 6 M sulphuric acid
2) 65% solution of mercury nitrate in 12 M nitric acid
3) 3% solution of nickel sulphate in distilled water
4) 4% solution of 1-nitroso-2-naphthol in 6 M nitric acid 1 mL of this mixture was pipetted into a 7 mL test tube with a 1 mL insert cap. 1 g of PVP K30 was then added, and the mixture shaken until a gel was formed. The test tube was capped, with the formulation being ready for use.

The formulation was found to be stable (i.e. no liquefying occurred) using an accelerated stability test well known in the art, where the temperature of the formulation was cycled between 50° C. and −50° C. on an hourly basis for 2 weeks (which is equivalent to a storage stability of about 2 years at ambient temperature). When the aged formulation was added to an aqueous sample, it completely dissolved in less than 60 seconds.

Example 1B 1 mL of the mixture of Example 1A was pipetted into a 7 mL test tube with a 1 mL insert cap. 1 g of Pluronic F88 was then added, and the mixture shaken until a gel was formed. The test tube was capped, with the formulation being ready for use.

Stability tests similar to those discussed above in Example 1A were conducted on the formulation, with similar results (i.e. stability and dissolving time) being obtained.

Example 2A

A formulation in accordance with another embodiment of the present invention was prepared by mixing 2 mL of component (1), 2.0 mL of (2), 1.0 mL of (3) and 0.1 mL of (4), where the components are as follows:
(1) 18% solution of mercury sulphate in 6 mol sulphuric acid
(2) 65% solution of mercury nitrate in 12 mol nitric acid
(3) 3% solution of nickel sulphate in distilled water
(4) 10% solution of cadmium sulphate in 6 mol nitric acid 1 mL of this mixture was pipetted into a 7 mL test tube with a 1 mL insert cap. 1 g of PVP K30 was then added, and the mixture shaken until a gel was formed. The test tube was capped, with the formulation being ready for use.

Stability tests similar to those discussed above in Example 1A were conducted on the formulation, with similar results (i.e. stability and dissolving time) being obtained.

Example 2B 1 mL of the mixture of Example 2A was pipetted into a 7 mL test tube with a 1 mL insert cap. 1 of Pluronic F88 was then added, and the mixture shaken until a gel was formed. The test tube was capped, with the formulation being ready for use.

Stability tests similar to those discussed above in Example 1A were conducted on the formulation, with similar results (i.e. stability and dissolving time) being obtained.

Example 3

Experiments were conducted to confirm the stability of formulations in accordance with the present invention under storage conditions, as well as their ability to rapidly disintegrate upon exposure to a urine sample. In these experiments, the stability and dissolution time of the gel was assessed visually, with the stability being assessed by confirming that the gel did not liquefy (i.e. before being mixed with the urine sample) when cycled between temperatures of between −50° C. and 50° C. on an hourly basis for 2 weeks. Total dissolution was defined as the time taken from mixing the formulation/urine sample and shaking for there to be no visible pieces of gel in the mixture.

Formulations containing the same mercury containing reagent, but different gel carriers were prepared, and their dissolution times and stability were assessed. The results are shown below in Table 1.

TABLE 1

| GEL CARRIER | DISSOLUTION TIME (SECS) | STABILITY (LIQUFYING) |
| --- | --- | --- |
| PVP K30 | 45 | NONE |
| PLURONIC F88 | 60 | NONE |
| PVPP | 90 | NONE |
| PAM SAP | 40 | NONE |
| CMC HV | 60 | NONE |

Example 4

In a clinical study the formulation of Example 1A was mixed with first pass midstream urine specimens from the patients discussed below, shaken and the colour of the resultant mixture assessed with reference to Table 2. The patients had separately been diagnosed for the specified conditions using conventional techniques (e.g. a colonoscopy for colorectal cancer), and this clinical study was conducted to assess the reliability of a formulation in accordance with the present invention.

Of 100 patients who had been diagnosed by known methods having colorectal cancers, 99 patients showed a strong positive result to the formulation, while one showed a weak positive result. This is equivalent to a 100% detection rate.

Of 36 patients who had been diagnosed with Breast Cancer by known methods, 33 patients showed strong positive result to the formulation, while two had weak positive results and one was negative. This is equivalent to a >97% detection rate.

Of 40 patients who had been diagnosed with Bladder Cancer by known methods, all of the patients showed a strong positive result to the formulation. This is equivalent to a 100% detection rate.

In these trials, the results were characterised into four categories: negative, weak positive, positive and strong positive. The relevant category was determined based on the colour which the formulation changed to after mixing with the patient's fluid sample, as shown in Table 2. The inventor has conducted extensive trials to confirm that the colours listed in Table 2 correlate with the recited quantity of tyrosine. A colour chart may also be provided to help distinguish between light red, red and bright red (although any form of positive result should prompt the patient to seek the advice of a registered medical practitioner for further testing).

TABLE 2

| COLOR | TYROSINE mg/ml | STANDARD |
| --- | --- | --- |
| Light Yellow | <3 | Negative |
| Light Red | 5 ± 1 | Weak Positive |
| Red | 10 ± 2 | Positive |
| Bright Red | 15 ± 2 | Strong Positive |

By way of comparison, 118 normal healthy people were tested during regular health checks, and the false positive rate was found to be lower than 2.54%.

Example 5

The ability of various absorbent materials to absorb and carry the mercury containing reagent, and then subsequently absorb urine, was tested in the manner described below. Firstly, the ability of various absorbent materials to absorb the reagent and urine solution under free swell conditions was assessed. Secondly, their ability to retain the reagent and urine when subsequently placed under pressure was assessed.

Materials:
  Absorbent material (see Table 3)
  Mercury-containing reagent (1 mL)—as per Example 1A
  Urine sample (5 mL)—separately analysed by HPLC and shown to contain about 2 mg/mL tyrosine, which is a normal amount of tyrosine in the urine of an adult male.

Equipment:
  Pyrex Vists 10 mL Griffin Low Form Glass Beaker with a height of 33 mm and an outer diameter of 25 mm
  Pyrex Buchner Funnel with Sintaglass disc (50 micron pore) 20 mm diameter
  Piston to fit the funnel (100 g, 19 mm diameter). Fit a sealing rubber ring to the piston to avoid leakage of liquid. This piston is designed to exert 0.5 psi pressure on test material held within the funnel.
  Balance (capable of measuring 0.001 g)
  Stopwatch
  Steel spatula
  Surgical gloves (to prevent moisture transfer)

Procedure:
A) Mercury-Containing Reagent
  1. Pre-wet the funnel with distilled water and drain thoroughly
  2. Place 1.0 g of the absorbent material into the sample tube and record weight as W1
  3. Add 1 ml mercury-containing reagent and record weight as W2
  4. Stand wetted absorbent material until reagent has been absorbed (1 minute)
  5. Transfer contents of sample tube to the Sintaglass funnel
  6. Allow non-absorbed mercury-containing reagent to drain into a pre-weighed tube (W3) for five minutes and record total weight as W4. Ensure all absorbent material has been transferred using the steel spatula
  7. Place the piston (without exerting pressure) on the remaining absorbent material
  8. Drain for further five minutes under the piston-load into the pre-weighted tube
  9. Measure the total weight of mercury-containing reagent in the pre-weighed tube along with any that has exuded past the piston and record as W5.
  10. Record visible appearance of the mercury-containing reagent on the absorbent material B) Urine on Absorbent Material Containing 1 mL Mercury-Containing Reagent (i.e. Prepared as per Method A))
1. Pre-wet the funnel with distilled water and drain thoroughly
2. Place the material with reagent in into the sample tube and record as R1
3. Add 5 ml urine and record as R2
4. Stand wetted material until the urine has been absorbed (2 minute)
5. Transfer contents of sample tube to the Sintaglass funnel
6. Allow non-absorbed urine to drain into a pre-weighed tube (R3) for five minutes and record total weight as R4. Ensure all material has been transferred using the steel spatula
7. Place the piston (without exerting pressure) on the remaining material
8. Drain for further five minutes under the piston-load into the pre-weighted tube
9. Measure the total weight of urine in the pre-weighed tube along with any that has exuded past the piston and record as R5.
10. Record visible appearance of urine on the absorbent material Calculations:
Reagent:
Free swell (g/g) is calculated as: (W2−[W4−W3])/W1
Retention (g/g) is calculated as: (W2−[W5−W3])/W1
Urine:
Free swell (g/g) is calculated as: (R2−[R4−R3])/R1
Retention (g/g) is calculated as: (R2−[R5−R3])/R1

TABLE 3

|  | Visual (after reagent) | Free Swell (after reagent) | Retention (after reagent) | Time (secs) for total absorption of reagent | Visual (after urine) | Free Swell (after urine) | Retention (after urine) | Time (secs) for total absorption of urine |
|---|---|---|---|---|---|---|---|---|
| Paper Pulp | Dry | 1 | 1 | 5 | Film on Top | 1.33 | 1.25 | 45 |
| Cotton Wool | Dry | 1 | 1 | 5 | Film on Top | 1.33 | 1.25 | 40 |
| Bleached Bamboo | Dry | 1 | 1 | 5 | Thick Film | 1.6 | 1.5 | 60 |
| Synthetic Microfiber | Dry | 1 | 1 | Instant | Dry | 1 | 1 | 30 |
| SAP Flock | Dry | 1 | 1 | Instant | Dry | 1 | 1 | 20 |
| PVA Flock | Dry | 1 | 1 | Instant | Dry | 1 | 1 | 20 |

These results show that the exemplified kinds of absorbent materials all very rapidly absorb the reagent with very little swelling and retain the reagent therein, even when subjected to significant amounts of pressure. The absorbent materials also rapidly (less than a min) absorb the urine. The colour of the absorbent material after it had absorbed the urine was a typical yellowish urine colour, as would be expected because the urine did not contain elevated levels of tyrosine.

Example 6

A number of clinical trials were conducted in order to confirm that the absorbent pads described herein are suitable carriers for a mercury-containing reagent and for use in the present invention. In these clinical trial, urine from a variety of patients was added to a container including 4-6 cells, in each of which resided an absorbent pad comprising a super-absorbent polymer. Some of the absorbent pads were placebos, as described above, other absorbent pads carried the mercury-containing reagent of Example 1A.

An 88 yo female presented with mild iron deficiency but normal haemoglobin levels. A FOBT (faecal occult blood test) had also returned a positive result. Her urine sample was analysed and returned appositive result (positive colour change in one of the cells), indicating a high risk of malignancy and therefore more urgent investigation was initiated. A colonoscopy showed that the patient had stage 1 colon cancer (adenocarcinoma).

A 57 yo patient presented with iron deficiency anaemia. Their CEA was normal and a CT scan of their abdomen/pelvis showed no acute distress. However, a mildly positive result was returned using the test of the present invention, indicating urgency for further investigation. A subsequent colonoscopy revealed large proximal transverse 8×3 cm polyp which was removed endoscopically. Histology revealed a small focus of moderately differentiated adenocarcinoma so surgery recommended to clear region. Subsequent right hemicolectomy revealed small residual cancer Stage 1

A 75 year old male patient with stage 3B colon cancer returned a positive FOB test as well as a positive result using the test of the present invention. An urgent colonoscopy was conducted, which revealed ulcerating sigmoid cancer requiring left hemicolectomy. Their CEA was also elevated 11 (0-5) and a CT scan showed sigmoid cancer and suspicious liver nodules, possibly metastases.

An 85 yo male presented with diarrhoea & weight loss. A CT scan showed sigmoid thickening with suspicious liver metastases. His urine was analysed and returned appositive result (positive colour change in one of the cells). Subsequent surgery confirmed metastatic peritoneal adenocarcinoma (stage 4).

A 73 yo male presented with anaemia and melena whilst on Xarelto for AF. He returned negative PET and CT scans. However, his urine was analysed and returned appositive result (positive colour change in one of the cells). A subsequent gastroscopy revealed 5 cm gastric adenocarcinoma and will undergo neo adjuvant chemotherapy before future surgery.

A 69 yo female presented with sudden weight loss & Iron deficiency anaemia. CT scans showed metastatic liver disease with omental metastases and right colonic wall thickening and possible renal cell cancer. Her urine was analysed and returned appositive result (positive colour change in one of the cells). A subsequent colonoscopy revealed right colon cancer—adenocarcinoma.

An 85 yo male with metastatic gallbladder cancer had an incidental tumour found by a CT scan performed because of new onset constipation. However, a follow up gall bladder polyp—colonoscopy was normal. The polyp grew in size from 4 mm to 25 mm over 18 mnths but was asymptomatic. However, his urine was analysed and returned appositive result (positive colour change in one of the cells). Surgery subsequently confirmed gallbladder adenocarcinoma.

A 58 yo male's urine returned a positive result (positive colour change in one of the cells). A subsequent colonoscopy revealed malignant looking rectal polyp, which was completely removed endoscopically with only a focus of adenocarcinoma. His CEA was normal, and a CT scan of his abdo/pelvis and an Mill of his rectum were all normal. His PSA was elevated 6.0 (0-3.5). Further investigation pending.

It will be appreciated that the present invention provides a number of new and useful results and advantages over existing diagnostic tests. For example, specific embodiments of the present invention may provide one or more of the following advantages:
- the mercury-containing reagent is safely contained within the gel or absorbent material;
- reliable results can be obtained due to the rapid mixing of the mercury-containing reagent and fluid sample (no second-guessing);
- the container does not necessarily need to be glass—plastic containers may be used (even if the mercury-containing reagent is highly acidic);
- the container can be provided in the form of a urine collection device, making it even simpler to use;
- regulatory approval is likely to be simpler to obtain because the test is only indicative of a potential disease or condition, with the patient needing to seek professional medical advice in the event of a positive result; and
- testing can be performed by people with relatively little (or no) medical training—e.g. the patient themselves.

It will be understood to persons skilled in the art of the present invention that many modifications may be made to the embodiments of the present invention specifically described above without departing from the spirit and scope of the invention. All such modifications are intended to fall within the scope of the following claims.

It will be also understood that whilst the preceding description refers to specific pieces of apparatus and equipment and sequences of method steps, these are provided for illustrative purposes only and are not intended to limit the scope of the present invention in any way.

It is to be understood that reference to any prior art publication referred to herein does not constitute an admission that that publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A formulation for detecting a species indicative of a disease in a patient, the formulation comprising:
   a mercury-containing reagent comprising mercury dissolved in an acid solution and which, when contacted with a fluid sample from the patient, colourimetrically indicates whether the fluid sample contains the species, wherein the mercury-containing reagent is contained within a non-flowing gel carrier which, upon exposure to the fluid sample, disintegrates and disperses into the fluid sample in less than 3 minutes to release substantially all of the mercury-containing reagent, thereby causing rapid mixing of the mercury-containing reagent and the fluid sample.

2. The formulation of claim 1, wherein the non-flowing gel carrier disintegrates to release substantially all of the mercury-containing reagent within less than about 1 minute after being exposed to the fluid sample.

3. The formulation of claim 1, wherein the non-flowing gel carrier has a viscosity of between about 50,000 and about 1,000,000 cps.

4. The formulation of claim 1 wherein the non-flowing gel carrier is a hydrogel.

5. The formulation of claim 1, wherein the non-flowing gel carrier is formed from any one of the following: polyacrylamides, carboxy methylcellulose, polyvinyl alcohol, poly(acrylamide-co-maleic acid), poly(vinylpyrrolidone), alginates, carbomers, polyoximers, natural and synthetic gums, and mixtures thereof.

6. The formulation of claim 1, wherein the formulation comprises between 20 and 80 vol % of the non-flowing gel carrier.

7. The formulation of claim 1, wherein the mercury-containing reagent comprises a source of $Hg^+$ ions and a source of $Hg^{2+}$ ions in an acid solution.

8. The formulation of claim 7, wherein the mercury-containing reagent further comprises one or more of the following: a source of $Ni^{2+}$ ions, a source of $Cd^{2+}$ ions, 1-nitroso-2-naphthol, a diazonium compound and an Azo compound.

9. The formulation of claim 1, wherein the formulation further comprises one or more of the following agents contained within the non-flowing gel carrier: dispersing agents, solubilising agents, wetting agents, emulsifying agents and combinations thereof.

10. The formulation of claim 1, wherein a volume of the formulation is provided in a unit form.

11. The formulation of claim 1, wherein the fluid sample is a urine sample from the patient.

12. The formulation of claim 1, further comprising a species indicative of a disease, wherein the species indicative of a disease in a patient is tyrosine.

13. The formulation of claim 12, wherein the disease is a cancer.

14. A kit for detecting a species indicative of a disease in a patient, the kit comprising:
   a mercury-containing reagent comprising mercury dissolved in an acid solution and which, when contacted with a fluid sample from the patient, colourimetrically indicates whether the fluid sample contains the species;
   a non-flowing gel carrier in which the mercury-containing reagent is contained but which, upon exposure to the fluid sample, disintegrates and disperses into the fluid sample in less than 3 minutes to release substantially all of the mercury-containing reagent, thereby causing rapid mixing of the mercury-containing reagent and the fluid sample; and
   a container in which the non-flowing gel carrier and the mercury-containing reagent is contained.

* * * * *